US009587283B2

(12) United States Patent
Niazi

(10) Patent No.: US 9,587,283 B2
(45) Date of Patent: Mar. 7, 2017

(54) INTERCONNECTED BIOREACTORS

(71) Applicant: Sarfaraz K. Niazi, Deerfield, IL (US)

(72) Inventor: Sarfaraz K. Niazi, Deerfield, IL (US)

(73) Assignee: Adello Biologics, Chicago, IL (US)

( * ) Notice: Subject to any disclaimer, the term of this patent is extended or adjusted under 35 U.S.C. 154(b) by 147 days.

(21) Appl. No.: 14/738,399

(22) Filed: Jun. 12, 2015

(65) Prior Publication Data
US 2015/0275318 A1  Oct. 1, 2015

Related U.S. Application Data

(63) Continuation of application No. 13/107,503, filed on May 13, 2011, now Pat. No. 9,068,215.

(51) Int. Cl.
*C12Q 3/00* (2006.01)
*C12M 1/00* (2006.01)
*C12M 3/06* (2006.01)

(52) U.S. Cl.
CPC ............... *C12Q 3/00* (2013.01); *C12M 23/14* (2013.01); *C12M 23/58* (2013.01); *C12M 27/16* (2013.01)

(58) Field of Classification Search
CPC ...... C12M 41/34; C12M 41/32; C12M 41/48; C12M 41/26; C12M 27/02; C12M 35/04; C12M 21/04; C12M 23/14; C12M 29/10; C12N 1/00
USPC ....................................... 435/289.1
See application file for complete search history.

(56) References Cited

U.S. PATENT DOCUMENTS

| | | | | |
|---|---|---|---|---|
| 7,816,138 B2 * | 10/2010 | Dutra | ...... | C12M 33/12 435/289.1 |
| 2005/0186669 A1 * | 8/2005 | Ho | ...... | C12M 27/16 435/287.1 |
| 2010/0261226 A1 * | 10/2010 | Niazi | ...... | C12M 23/26 435/40 |
| 2012/0100576 A1 * | 4/2012 | Goletz | ...... | C12M 23/14 435/70.1 |

* cited by examiner

*Primary Examiner* — Michael Hobbs
(74) *Attorney, Agent, or Firm* — Adello Biologics, LLC; Sarfaraz K. Niazi; Cheryl Liljestrand

(57) ABSTRACT

A method of homogenously mixing the contents of a plurality of bioreactors by providing a receiving container capable of holding an appropriate quantity of the liquid and repeatedly raising and lowering the receiving container to a position above or below the position of the bioreactors resulting in mixing the contents of the bioreactors.

6 Claims, 5 Drawing Sheets

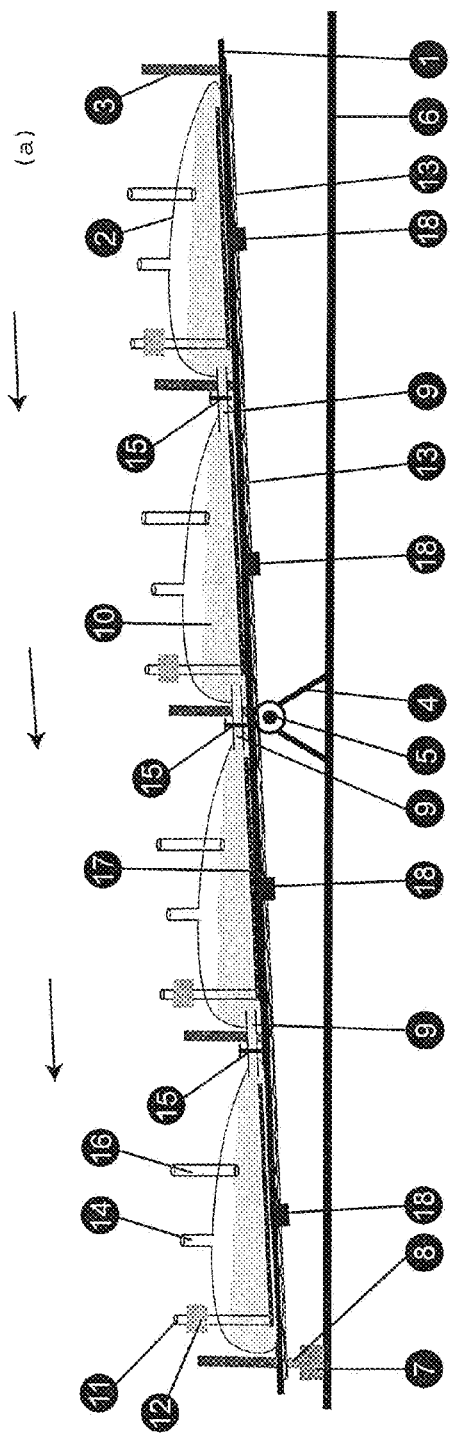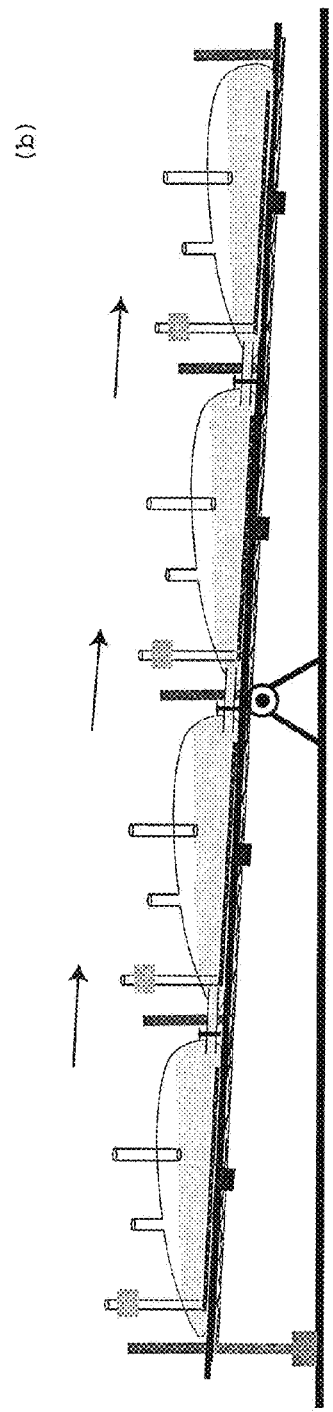
Figure 1

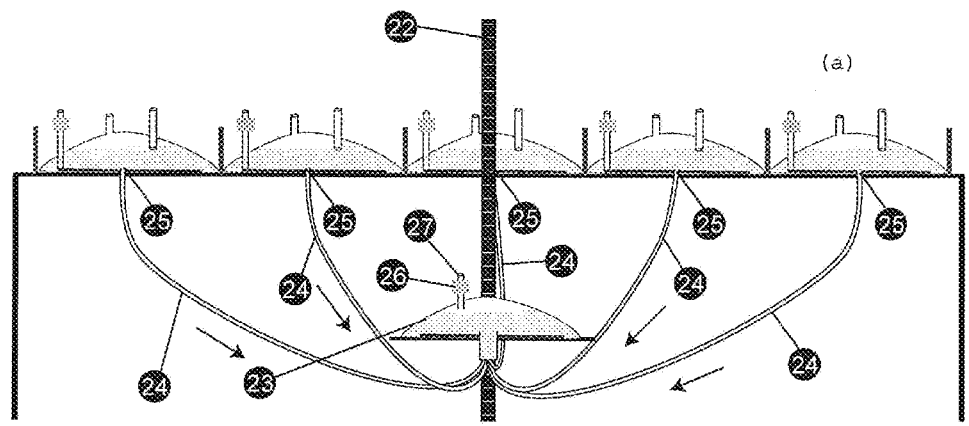
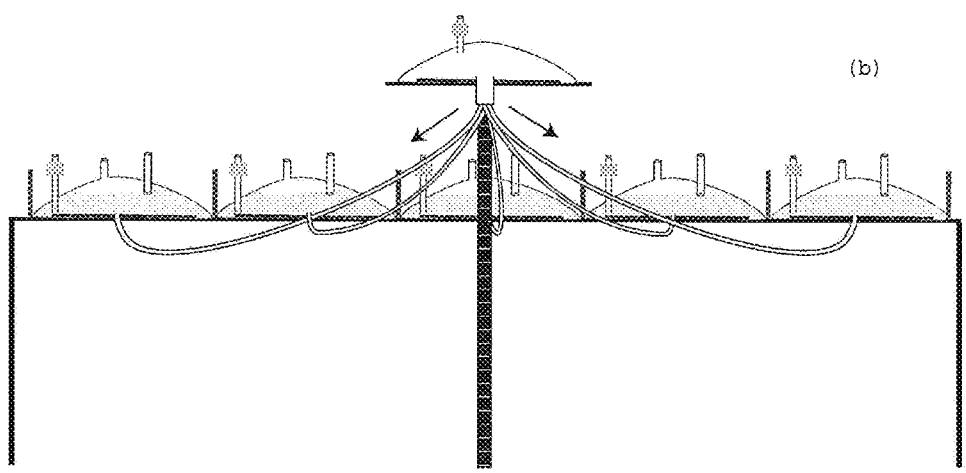
Figure 5

INTERCONNECTED BIOREACTORS

CROSS REFERENCE TO RELATED APPLICATION

This application is a continuation of U.S. patent application Ser. No. 13/107,503, now U.S. Pat. No. 9,068,215, entitled "Interconnected Bioreactors" filed on May 13, 2011, the contents of which are incorporated herein by reference in its entirety.

FIELD OF THE INVENTION

The instant invention relates generally to the field of bioreactor design wherein a multiple of bioreactors are used to generate a single large production batch.

BACKGROUND OF THE INVENTION

A pharmaceutical production batch size is defined in accordance with the CFR21 (Code of Federal Register) as a homogenous mixture of ingredients. A "batch" or "lot" as defined in the WHO GMP guideline (TRS 908 Annex 4) as "a defined quantity of starting material, packaging material, or product processed in a single process or series of processes so that it is expected to be homogeneous.

It may sometimes be necessary to divide a batch into a number of sub-batches, which are later brought together to form a final homogeneous batch. In the case of terminal sterilization, the batch size is determined by the capacity of the autoclave. In continuous manufacture, the batch must correspond to a defined fraction of the production, characterized by its intended homogeneity. The batch size can be defined either as a fixed quantity or as the amount produced in a fixed time interval".

In those instances where smaller sub-batches are manufactured and pooled together, it requires combining them in a larger container wherein the sub-batches can be mixed to a homogenous mixture. However, in many situations, a larger container use can be prohibitive such as in clean rooms and thus there is an unmet need to invent systems that will allow mixing between containers without the need to mix the entire content in a larger container.

The idea of mixing contents of multiple containers also offers many significant financial and regulatory advantages.

The science of pharmaceutical manufacturing teaches us that changing the size of a batch is not a simply exercise. As the size of a batch changes, the dynamics of mixing also changes along with the dynamics of any reactions taking place in the manufacturing process and as a result a manufacturer is required to conduct studies to validate the conditions of manufacturing to assure that a specific size of a batch would consistently result in the same product. Therefore manufacturers are required to invest substantial time and money in validating different batch sizes to meet their need for specific quantities of the product.

Biological manufacturing of drugs using bioreactors even faces greater challenges as changes in the volume of liquid (nutrient media and biological culture) in the bioreactor container significantly changes the conditions required to produce a product consistently. The factors that are of significant importance include the geometry of the container, the amount of gasification, the amount and the nature of agitation of the liquid and as a result it is not possible to predict the behavior of manufacturing process unless it is practiced and appropriate corrections made to various parameters of the manufacturing process.

Since the manufacturers of drugs are often faced with a choice of making a larger or a smaller batch at a time, the most obvious exercise conducted is to validate several batch sizes and use a specific batch size based on the current need of manufacturing. The use of different batch sizes also require making available different size of vessels, and other technical attachments to a bioreactor, making the cost of maintaining several validated batch sizes very high. However, as biological products are most expensive to manufacture and often have a shorter shelf-life, it is inevitable for the manufacturers not to maintain several validated batch sizes.

Since bioreactors mainly employ liquid contents, they are easier to mix and finding a solution to mix the contents of several bioreactors in a manner that it would meet the requirement of the FDA in accordance with CFR21 for a single batch would reduce the cost of manufacturing significantly by reducing the number of batches that need to be validated and affording the flexibility to manufacturers to produce different sizes of batches at will using fewer variations in the manufacturing equipment.

There is no prior art that teaches on combining the contents of several bioreactors in such manner as to constitute a single batch. The instant invention not only resolves this critical hurdle in reducing the cost of production but also teaches a commercial level applications where hundreds and thousands of liters of liquid can be processed using low-cost solution to mix liquids.

SUMMARY OF THE INVENTION

Bioreactors are used to grow a cell culture or biological organisms, often genetically modified, in a nutrient media to express a target chemical or protein of clinical importance. Given the inherent variability of the biological processes, an extensive validation of the manufacturing process is required for cGMP manufacturing of these expressed molecules.

The process of validation requires a detailed analysis of the parameters fixed for the production of a batch and conducting a Process Analytical Testing (PAT) wherein various conditions applied to manufacturing are varied until an unacceptable limit is reached to justify the internal control limits and their ranges. The process of validation is perhaps the most expensive part of cGMP production of drugs. Where multiple batch sizes are validated, the cost multiplies and often times it becomes too prohibitive for a manufacturer to produce several sizes of batches. The cost of stocking different sizes of equipment further makes it prohibitive for many small manufacturers to enter the field of biological manufacturing.

There is a large unmet need to create a method wherein a single validated batch size can be used to manufacture unlimited sizes of batches by connecting several validated smaller batches to produce an infinitely variable batch size. It is important that the method meet the requirements of the definition of a batch as provided in CFR21.

The instant invention resolves the major cost barrier in the production of biological drugs by teaching methods of mixing the contents of several bioreactors by recirculating the liquid contents and thus constituting a larger single batch. While transferring liquid contents from one bioreactor container to another can be achieved by such established methods as using a peristaltic pump to avoid contamination from the environment, this method is not practical for large-scale production. The instant invention offers a most cost-effective solution to resolve this problem as well.

A physical model of the transport of liquids from one container to another is analogous to a physical clearance and equilibration model; for the contents to be declared as homogenously mixed, the contents should be moved back and for sufficient times to achieve homogeneity. The rate of equilibration to achieve homogeneity is easily calculated by the rate constant of the liquid trans to and from each container. Assuming that that the liquid in two bioreactors is transferred back and forth at the same rate simultaneously then the rate constant for equilibration is simply the ratio of the volume transferred per unit of time.

As an example, if 10 L of liquid is transferred between two bioreactors per minute, each containing 100 L of liquid, K value is 0.1 and based on the exponential nature of equilibration, the half-life of equilibration would be 0.693/K or 6.93 minutes. To achieve a 99% equilibration, approximately seven half lives are needed or about 50 minutes of continuous mixing comprising transporting within each minute 10 L of liquid from one container to the other container.

The instant invention teaches several methods of achieving equilibration of the contents of several bioreactors arranged such that the contents of one bioreactor would readily flow into the next bioreactor or to a common vessel under gravity effect only.

One embodiment arranges bioreactors on a flat surface and moves the surface in a seesaw manner so that in the first position, the liquid flows from one bag to the and when the position is reversed; it flows back to the bioreactors. Since the complete cycle of transfer takes completion of both stages, the K value is one-half of the flow rates from one bioreactor to another. For example, if 10 L of liquid is transferred per minute in each direction, then it takes two minutes to complete the cycle and the K value is 0.05 and the half life is 0.693/0.05 or about 14 minutes and the time for 99% equilibration is 88 minutes.

The same calculations will apply to other methods of transferring the liquid form one container to another, for example, if the bioreactors are raised or lowered to start the flow and then the position of bioreactors reversed or if the amount of liquid transferred is collected in a separate bag, which is then raised to return the liquid to the bioreactors.

The above calculations assume that at any given time the contents in each bioreactor are homogenous at all times; it is reasonable to assume that a certain period of time would be needed, depending on the operational conditions of the bioreactors, to achieve homogeneity within the bioreactor and that will change the total time needed to achieve a homogeneity among all connected bioreactors.

In most instances, the transfer of liquid from one bioreactor to another need not be a fast process and can be allowed to go on slowly throughout the manufacturing operations. Alternately, the mixing of contents among the bioreactors is attempted at the end of the bioreaction cycle, at the beginning and at the end or intermittently. Of greatest importance is the guarantee of homogenous mixing at the end of bioreaction cycle, before the liquid in the bioreactor is removed from bioreactors for further processing.

BRIEF DESCRIPTION OF THE DRAWINGS

FIG. 1 shows the method of mixing using a seesaw arrangement of bioreactors allowing back and forth movement of liquid among the bioreactors arranged in a series. The arrows indicate the direction of flow of liquid.

FIG. 5 shows the method of mixing where bioreactors contents flow into a common empty container under gravity flow and the empty container is raised above the bioreactors to return the contents to the bioreactors. The arrows indicate the direction of flow of liquid.

DETAILS OF THE INVENTION

Figure 2:
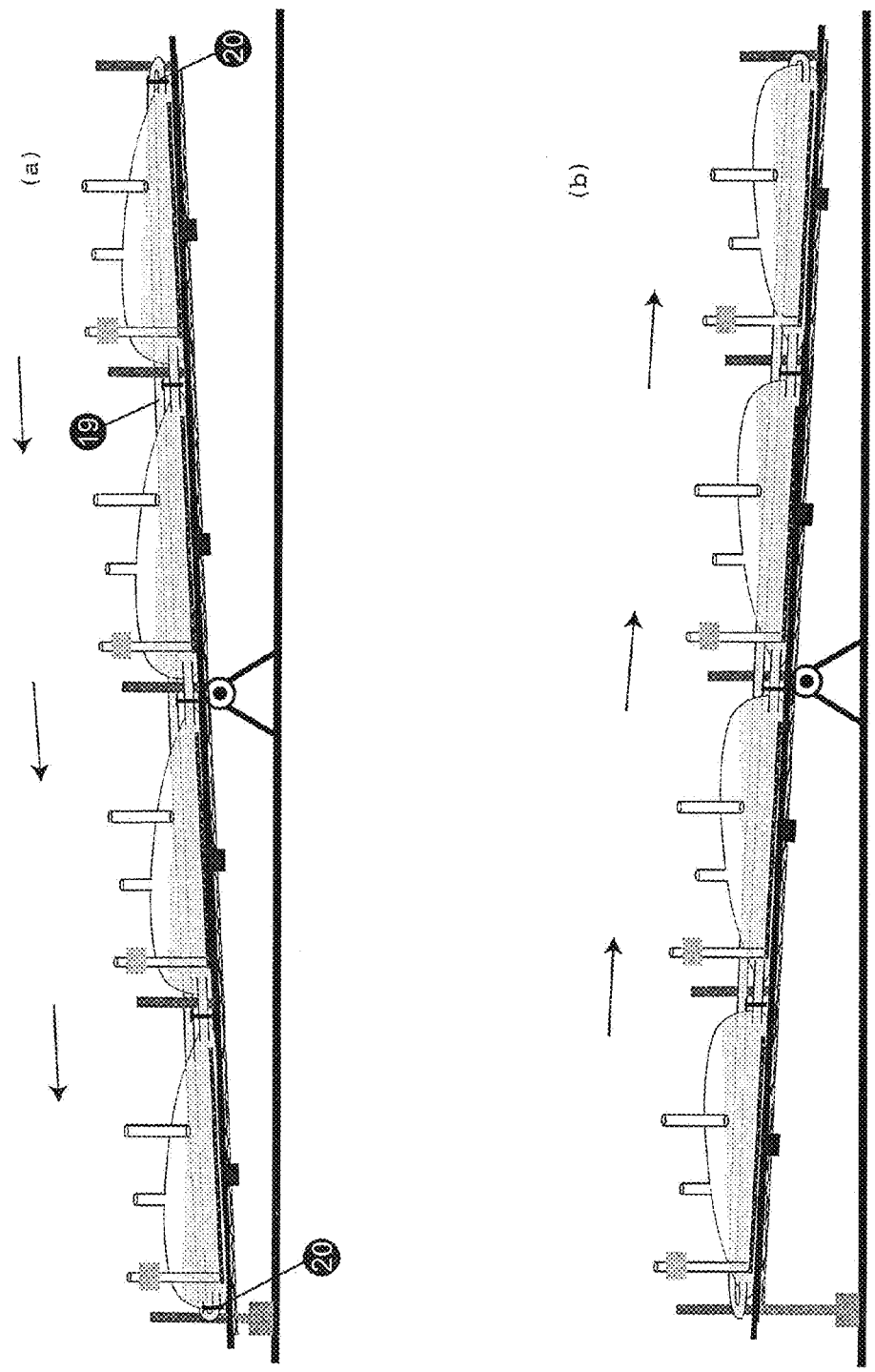
FIG. 2 shows the method of mixing of FIG. 1 except that the liquid from the last bioreactor is transferred to the first bioreactor and the liquid flows only in one direction. The arrows indicate the direction of flow of liquid.

Validation of biological manufacturing process is an extremely expensive exercise to manufacture drugs under cGMP (Current Good Manufacturing Practice) conditions. The instant invention allows use of a single validated batch size of manufacturing to produce batches of any size requiring only a mixing validation, which is much easier and least expensive exercise to conduct. One way of doing this would be to collect the contents from several bioreactors in a single large vessel, mixing it thoroughly and processing it as a single batch. However, this would require providing a larger container that must also be sterile and the conditions of mixing validated for every batch size planned. In most instances this would be an impractical exercise where extremely large batches are planned.

Today, batch sizes of hundreds and thousands of liters are commonly produced and whereas it is practical to arrange, for example, several 500 L bioreactors in a room, providing a 5000 L container to mix the contents of 10 such bioreactors may not be feasible.

The most practical and useful solution to making a large homogeneous batch is to circulate the liquid among the smaller bioreactors arranged in a daisy chain where the liquid inside the bioreactors flow under gravity, removing the need to use additional equipment. Incidentally, the only equipment that can be used otherwise is a peristaltic pump as this offers liquid transfer without exposing it to the environment or causing any contamination. Large peristaltic pumps are expensive and difficult to operate and additionally affect the biological culture as the liquid is squeezed through a tube whether this additional modification to the condition of bioreaction would require further validation remains debatable, the regulatory agencies might make this a requirement. It is therefore advisable to avoid using any pump to transfer the liquid among the bioreactors.

A back and forth mixing of the liquid in the bioreactors requires a system where the effect of gravity can be reversed and this is achieved by changing the vertical position of the bioreactors either in a seesaw arrangement or simply by raising the bioreactors held on a platform. Another novel approach is to use a single path of flow wherein the last bioreactors transfers the added liquid back to the first bioreactor or even replacing the first and the last bioreactors with empty containers used only for the transfer of liquid either back and forth or in one direction.

Another novel method is to simply allow the bioreactors arranged at the same plane to flow into an empty container held at a lower position and when it reaches a certain weight, raising the container to return the liquid back to the bioreactors. For additional assurance, the contents in the receiving containers can be kept mixed continuously by shaking the container.

FIG. 1 shows a preferred embodiment wherein the bioreactors are moved up and down in a seesaw movement. 1: Hard platform; 2: Bioreactor; 3: Flapper for agitation; 4: Fulcrum stand; 5: Ball bearing for fulcrum stand; 6: Base support platform; 7: Hydraulic lift motor; 8: Hydraulic lift shaft; 9: Liquid flow ports; 10: Liquid in bioreactor; 11: gas inlet; 12: gas sterilizing filter; 13: heating element; 14: gas outlet; 15: liquid port closers; 16: nutrient media inlet/outlet; 17: gas sparging rod; 18: weight sensor. The arrows indicate the direction of flow.

FIG. 1 (*a*) represent a position of hard platform wherein the liquid is flowing from right to left through the liquid ports between the bioreactors; FIG. 1(*b*) shows a position of hard platform wherein the liquid is flowing from left to right through the liquid ports between the bioreactors.

The system is operated by introducing nutrient media and biological culture in the bioreactor container, turning on the heating element, starting agitation, starting gassing and when ready to start mixing of liquid content among the bioreactors, opening the closure of the liquid ports, raising one side of the hard platform so that the liquid begins to flow across all bioreactors, resulting in accumulation of liquid in the last bioreactor container; the direction of flow is then reversed when a certain weight increase is achieved in the last bioreactor; reversing the flow equalizes the original weight of all containers and the process is repeated at a pre-determined frequency to assure homogeneous mixing.

In an more specific example, 100 L of liquid is present in each bioreactor and 10 L of liquid is moved in the first cycle resulting in 90 L liquid in the first container and 110 L liquid in the last container; upon reversing the process, all container regain their original volume of 100 L.

FIG. 2 shows the preferred embodiment of FIG. 1 with additional elements 19: liquid port closer; 20: liquid port between 1st and nth bioreactor.

FIG. 2(*a*) represent a position of hard platform wherein the liquid is flowing from right to left through the liquid ports between the bioreactors; FIG. 2(*b*) represent a position of hard platform wherein the liquid is flowing from left to right through the liquid ports between the two bioreactors at the end of chain on both sides and not between adjacent bioreactors. The system is operated as described above in FIG. 1 except that before reversing the flow, all liquid ports are closed except the one between the first and the last bioreactor resulting in a circulation of liquid among all containers.

Figure 3:
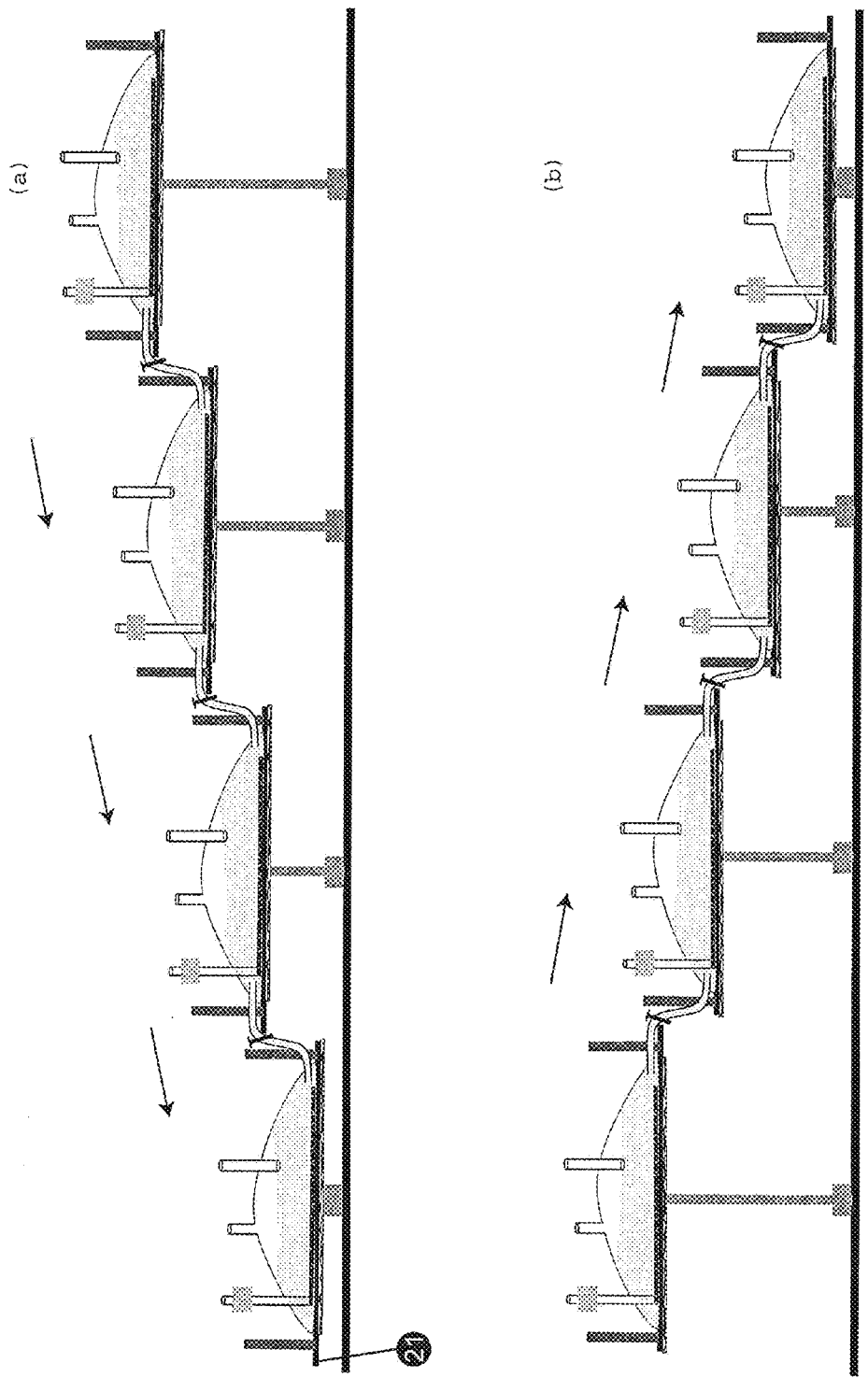
FIG. 3 shows the method of mixing where bioreactors are moved up and down to begin the flow from one container to another and by reversing the vertical position of bioreactors, causing back flow in the reverse direction. The arrows indicate the direction of flow of liquid.

FIG. 3 describes all features in FIG. 1 with additional feature 21: Movable hard platform that allows the support of each bioreactor to move up and down independently. The systems is operated as identically shown in FIG. 1 except that in place of raising the platform at one edge, the bioreactors are moved up or down to create a cascade formation. FIG. 3(*a*) shows the flow rate from right to left and FIG. 3(*b*) shows the flow from left to right.

Figure 4:
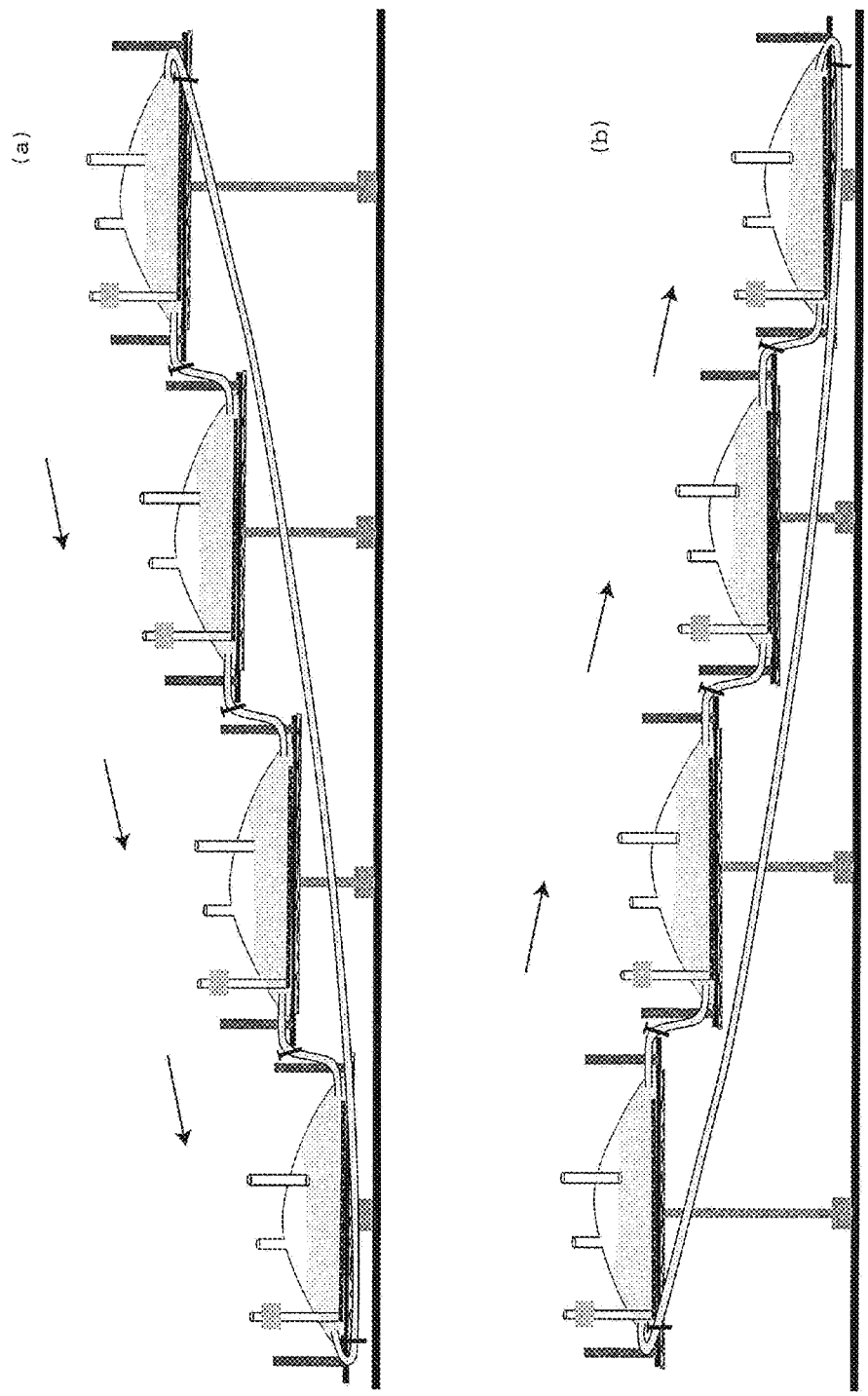
FIG. 4 shows the method of mixing according to FIG. 4 except that the liquid from the last bioreactor is transferred to the first bioreactor and the liquid flows only in one direction. The arrows indicate the direction of flow of liquid.

FIG. 4 describes all features in FIG. 3 wherein the system is operated by closing all liquid ports except the one between the first and the last bioreactor resulting in a complete circulation of liquid among the bioreactors. FIG. 4(*a*) shows the flow of liquid from left to right through each bioreactor and FIG. 4(*a*) shows the flow from the last bioreactor on the left to the first bioreactor on the right.

FIG. 5 shows all features of FIG. 1 except the feature 9 (liquid ports) and 15 (liquid port closure systems) with additional elements 22: vertical support for moving the receiving container; 23: receiving container; 24: drain tube; 25: liquid drain port; 26: sterilizing gas filter; 27: gas outlet.

FIG. 5(*a*) shows a position where the receiving container is lowered to receive the liquid from bioreactors; FIG. 5(*b*) shows a position where the receiving container is raised to such level as to return the liquid from the receiving container back to the bioreactors.

The system is operated by allowing liquid to drain under gravity in a container placed below the plane of the bioreactors; all drain tubes enter a single vertical tube allowing mixing of contents prior to entering the receiving container; when the receiving container has reached a certain pre-determined weight, the receiving container is raised above the plane of the bioreactor causing a backflow of liquid to all bioreactors.

The components of the liquid port described herein, which come into contact with the liquid thereby desirably, comprise biocompatible materials, more desirably biocompatible polymers, and are preferably sterilizable.

It should also be understood that many of the components described herein also are desirably flexible, e.g., the containers desirably comprise flexible biocompatible polymer containers (such as collapsible bags), with the conduits also desirably comprising such biocompatible polymers. The flexible material is further desirably one that is USP Class VI certified, e.g., silicone, polycarbonate, polyethylene, and polypropylene. Non-limiting examples of flexible materials include polymers such as polyethylene (e.g., linear low density polyethylene and ultra low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. If desired, portions of the flexible container may comprise a substantially rigid material such as a rigid polymer (e.g., high density polyethylene), metal, and/or glass.

All methods used for raising or lowering the bioreactors require a mechanical method and several methods are readily available in the art; these may include using an electrical motor, a hydraulic device, an air-driven device or any other such method, the choice of which is not limiting in the instant invention.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of homogenously mixing the contents of a plurality of bioreactors comprising:
   a. providing a hard platform to support a plurality of bioreactors;
   b. providing a fulcrum stand to support the hard platform and allow movement of the hard platform to a pre-determined angle on either side of the stand, wherein the platform is capable of being raised or lowered;
   c. installing a plurality of bioreactors, 1 though n, in a series on the hard platform, wherein each bioreactor comprises at least two liquid ports wherein the port comprises a valve for opening or closing the port and at least one sensor, wherein the sensor is capable of measuring the weight of the bioreactor;
   d. connecting one liquid port of the first bioreactor in the series of bioreactors to one liquid port of the next bioreactor in the series, and continuing the connectivity till the nth bioreactor in the series is connected;
   e. closing the second liquid port of the first bioreactor and the second liquid port of the nth bioreactor;
   f. raising the hard platform at one end to a sufficient height to allow flow of the liquids of the bioreactors across all bioreactors;
   g. measuring the increase in the weight of the nth bioreactor to a pre-determined level;
   h. lowering the same end of the hard platform to the same degree as the platform was raised in step (f);
   i. measuring the increase in the weight of the first bioreactor to a pre-determined level; and
   j. repeating steps (e) to (i) periodically or continuously.

2. A method of homogenously mixing the contents of a plurality of bioreactors comprising:
   a. providing a hard platform to support a plurality of bioreactors;
   b. providing a fulcrum stand to support the hard platform and allow movement of the hard platform to a pre-determined angle on either side of the stand, wherein the platform is capable of being raised or lowered;
   c. installing a plurality of bioreactors, 1 though n, in a series on the hard platform, wherein each bioreactor comprises at least two liquid ports wherein the port comprises a valve for opening or closing the port and at least one sensor, wherein the sensor is capable of measuring the weight of the bioreactor;
   d. connecting one liquid port of the first bioreactor in the series of bioreactors to one liquid port of the next bioreactor in the series, and continuing the connectivity till the nth bioreactor in the series is connected;
   e. connecting the second liquid port of the first bioreactor with the second port of the nth bioreactor;
   f. closing the second liquid port of the first bioreactor and the second liquid port of the nth bioreactor;
   g. raising the hard platform at one end to a sufficient height to allow flow of the liquids of the bioreactors across all bioreactors;
   h. measuring the increase in the weight of the nth bioreactor to a pre-determined level;
   i. closing all liquid ports except the second liquid port of the nth bioreactor and the second liquid port of the first bioreactor;
   j. lowering the same end of the hard platform to the same degree as the platform was raised in step (f);
   k. measuring the increase in the weight of the first bioreactor to a pre-determined level;
   l. repeating the steps (f) to (k) periodically or continuously.

3. A method of homogenously mixing the contents of a plurality of bioreactors comprising:
   a. providing a hard individual platform to support each of a plurality of bioreactors wherein each platform is capable of being individually raised and lowered;
   b. installing a plurality of bioreactors, 1 though n, in a series on the individual platforms, wherein each bioreactor comprises at least two liquid ports wherein the port comprises a valve for opening or closing the port and at least one sensor, wherein the sensor is capable of measuring the weight of the bioreactor;
   c. connecting one liquid port of the first bioreactor in the series of bioreactors to one liquid port of the next bioreactor in the series, and continuing the connectivity till the nth bioreactor in the series is connected;
   d. closing the second liquid port of the first bioreactor and the second liquid port of the nth bioreactor;
   e. arranging the individual platforms in a cascade formation such that the bioreactors are elevated with equal vertical distance between each bioreactor;
   f. opening all liquid ports except the second liquid port of the first bioreactor and the second liquid port of the nth bioreactor;
   g. raising the first bioreactor platform to the highest position and the nth bioreactor platform to the lowest position to allow flow of the liquids of the bioreactors across all bioreactors;
   h. measuring the increase in the weight of the nth bioreactor to a pre-determined level;
   i. reversing the order of elevation of bioreactor platforms, with the first bioreactor platform being at the lowest level and the nth bioreactor platform at the highest level;
   j. measuring the increase in the weight of the first bioreactor to a pre-determined level;
   k. repeating the steps (d) to (j) periodically or continuously.

4. A method of homogenously mixing the contents of a plurality of bioreactors comprising:
   a. providing a hard individual platform to support each of a plurality of bioreactors wherein each platform is capable of being individually raised and lowered;
   b. installing a plurality of bioreactors, 1 though n, in a series on the individual platforms, wherein each bioreactor comprises at least two liquid ports wherein the port comprises a valve for opening or closing the port and at least one sensor, wherein the sensor is capable of measuring the weight of the bioreactor;

c. connecting one liquid port of the first bioreactor in the series of bioreactors to one liquid port of the next bioreactor in the series, and continuing the connectivity till the nth bioreactor in the series is connected;
d. connecting the second liquid port of the first bioreactor to the second liquid port of the nth bioreactor;
e. closing the second liquid port of the first bioreactor and the second liquid port of the nth bioreactor;
f. arranging the individual platforms in a cascade formation such that the bioreactors are elevated with equal vertical distance between each bioreactor;
g. opening all liquid ports;
h. raising the first bioreactor platform to the highest position and the nth bioreactor platform to the lowest position to allow flow of the liquids of the bioreactors across all bioreactors;
i. measuring the increase in the weight of the nth bioreactor to a pre-determined level;
j. closing all liquid ports except the second liquid port of the nth bioreactor and the second liquid port of the first bioreactor;
k. raising the nth bioreactor platform to a position higher than the first bioreactor platform;
l. measuring the increase in the weight of the first bioreactor to a pre-determined level;
m. repeating the steps (e) to (k) periodically or continuously.

5. The method of claim 4, wherein the bioreactors are arranged vertically, and wherein the first liquid port is installed at the bottom surface of the bioreactor and the second liquid port is installed at the top surface of the bioreactor.

6. The method of homogenously mixing the contents of a plurality of bioreactors according to any one of claims 1-5, wherein the first and the last bioreactor is an empty receiving container capable of holding a volume of liquid recalculated within the bioreactors, generally about $1/10$ to $1/5$ of the volume in each bioreactor.

* * * * *